United States Patent
Morgenstern et al.

(10) Patent No.: US 11,224,244 B2
(45) Date of Patent: *Jan. 18, 2022

(54) **STRAINS OF *LACTOBACILLUS* WITH ANTIFUNGAL PROPERTIES**

(71) Applicant: DUPONT NUTRITION BIOSCIENCES APS, Copenhagen (DK)

(72) Inventors: Heike Ursula Morgenstern, Rønde (DK); Connie Benfeldt, Brabrand (DK)

(73) Assignee: DUPONT NUTRITION BIOSCIENCES APS

( * ) Notice: Subject to any disclaimer, the term of this patent is extended or adjusted under 35 U.S.C. 154(b) by 0 days.

This patent is subject to a terminal disclaimer.

(21) Appl. No.: 15/662,909

(22) Filed: Jul. 28, 2017

(65) Prior Publication Data

US 2018/0020673 A1    Jan. 25, 2018

Related U.S. Application Data

(63) Continuation of application No. 15/380,213, filed on Dec. 15, 2016, now abandoned, which is a continuation of application No. 14/402,625, filed as application No. PCT/EP2013/060370 on May 21, 2013, now abandoned.

(60) Provisional application No. 61/649,651, filed on May 21, 2012.

(51) Int. Cl.

| A23L 29/00 | (2016.01) |
|---|---|
| A23C 9/12 | (2006.01) |
| A23C 9/123 | (2006.01) |
| A23C 19/032 | (2006.01) |
| A23C 19/10 | (2006.01) |
| A23L 3/3463 | (2006.01) |
| A01N 63/20 | (2020.01) |
| C12N 1/20 | (2006.01) |
| C12R 1/25 | (2006.01) |
| C12R 1/225 | (2006.01) |

(52) U.S. Cl.
CPC ............ *A23L 29/065* (2016.08); *A01N 63/20* (2020.01); *A23C 9/12* (2013.01); *A23C 9/123* (2013.01); *A23C 19/0321* (2013.01); *A23C 19/0323* (2013.01); *A23C 19/10* (2013.01); *A23L 3/3463* (2013.01); *C12N 1/20* (2013.01); *C12N 1/205* (2021.05); *A23Y 2220/63* (2013.01); *A23Y 2220/67* (2013.01); *C12R 2001/225* (2021.05); *C12R 2001/25* (2021.05)

(58) Field of Classification Search
CPC ..... A01N 63/10; A23L 29/065; A23L 3/3463; C12N 1/20; A23C 19/10; A23C 19/0323; A23C 19/0321; A23C 9/123; A23C 9/12; A23C 9/127; C12R 1/225; C12R 1/25; A23Y 2220/67; A23Y 2220/63; A23V 2002/00

See application file for complete search history.

(56) References Cited

U.S. PATENT DOCUMENTS

| 3,794,739 | A | | 2/1974 | Lee et al. |
|---|---|---|---|---|
| 4,728,516 | A | | 3/1988 | Boudreaux et al. |
| 4,734,361 | A | | 3/1988 | Murao et al. |
| 5,173,319 | A | | 12/1992 | Boudreaux et al. |
| 5,338,682 | A | * | 8/1994 | Sasaki .................. A23C 9/1234 426/42 |
| 5,378,458 | A | | 1/1995 | Maeyrae-Maekinen et al. |
| 5,989,612 | A | * | 11/1999 | King ........................ A21D 8/04 426/335 |
| 6,316,067 | B1 | * | 11/2001 | Edwards ................. B32B 27/08 428/34.9 |
| 7,780,970 | B2 | | 8/2010 | Schlothauer et al. |
| 7,919,277 | B2 | | 4/2011 | Russell et al. |
| 7,927,639 | B2 | | 4/2011 | Schwenninger et al. |
| 8,361,725 | B2 | | 1/2013 | Russell et al. |
| 8,557,561 | B2 | | 10/2013 | Chambaud et al. |
| 8,563,295 | B2 | | 10/2013 | Davis et al. |
| 9,011,877 | B2 | | 4/2015 | Davis et al. |
| 9,402,871 | B2 | | 8/2016 | Davis et al. |
| 9,439,445 | B2 | | 9/2016 | Perrier et al. |
| 9,629,388 | B2 | * | 4/2017 | Benfeldt ................. A23C 9/127 |
| 2005/0095318 | A1 | * | 5/2005 | Schwenninger ....... A01N 63/00 426/61 |
| 2007/0298080 | A1 | | 12/2007 | Desreumaux et al. |

(Continued)

FOREIGN PATENT DOCUMENTS

| DE | 202006014937 U1 | 11/2006 |
|---|---|---|
| EP | 0302300 A2 | 2/1989 |

(Continued)

OTHER PUBLICATIONS

Bernardeau, M et al. Beneficial lactobacilli in food and feed: long-term use, biodiversity and proposals for specific and realistic safety assessments. FEMS Microbiol. Rev. 2006. 30: 487-513. (Year: 2006).*

(Continued)

*Primary Examiner* — Renee Claytor
*Assistant Examiner* — Susan E. Fernandez

(57) ABSTRACT

The present invention relates to novel strains of *Lactobacillus* as well as preparations and compositions, such as fermentation broths, protective cultures, final food or feed product with *Lactobacillus* alone or in combination with bacteria of the genus *Propionibacterium*. The present invention further relates to methods for the controlling of growth of a contaminant, such as a bacteria, yeast or mould by using these novel strains of *Lactobacillus*.

15 Claims, 4 Drawing Sheets

(56) References Cited

U.S. PATENT DOCUMENTS

Figure 1:
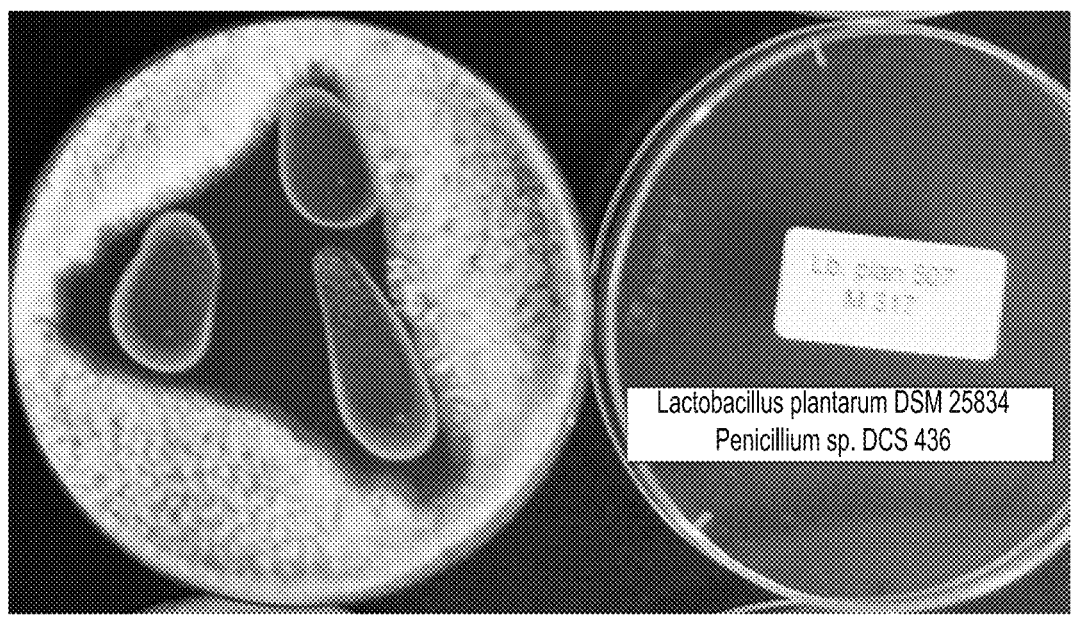

| | | |
|---|---|---|
| 2008/0286406 A1 | 11/2008 | Miyamoto et al. |
| 2008/0299098 A1 | 12/2008 | Se et al. |
| 2009/0311227 A1 | 12/2009 | Ouwehand et al. |
| 2011/0045134 A1 | 2/2011 | Perrier et al. |
| 2013/0158245 A1 | 6/2013 | Russell et al. |
| 2015/0023936 A1 | 1/2015 | Desreumaux et al. |
| 2015/0056628 A1 | 2/2015 | Russell et al. |
| 2018/0036355 A1 | 2/2018 | Desreumaux et al. |

FOREIGN PATENT DOCUMENTS

| | | |
|---|---|---|
| EP | 0576780 A3 | 1/1995 |
| EP | 1308506 A1 | 5/2003 |
| EP | 1530642 A2 | 5/2005 |
| EP | 1740726 A2 | 1/2007 |
| EP | 1796698 A1 | 6/2007 |
| EP | 2245943 A1 | 11/2010 |
| WO | 2003/040349 A1 | 5/2003 |
| WO | 2004/013343 A2 | 2/2004 |
| WO | 2006/032542 A1 | 3/2006 |
| WO | 2006/073445 A2 | 7/2006 |
| WO | 2007/132359 A2 | 11/2007 |
| WO | 2009/102143 A2 | 8/2009 |
| WO | 2009/130423 A2 | 10/2009 |
| WO | 2010/081138 A1 | 7/2010 |

OTHER PUBLICATIONS

Siezen, RJ et al. Genomic diversity and versatility of Lactobacillus plantarum, a natural metabolic engineer. Microbial Cell Factories. 2011. 10(Suppl. 1): 53. 13 pages. Published online Aug. 30, 2011. (Year: 2011).*

Chervaux, C et al. Physiological study of *Lactobacillus delbrueckii* subsp. *bulgaricus* strains in a novel chemically defined medium. Applied and Environmental Microbiology. 2000. 66(12): 5306-5311. (Year: 2000).*

Wang et al., "Production and Characterization of Antifungal Compounds Produced by Lactobacillus Plantarum IMAU10014," PLoS ONE, 2012, vol. 17, No. 1, pp. 1-7.

Tolvanen et al., "Survival of Listeria Monocytogenes Strains in a Dry Sausage Model," Journal of Food Protection, 2008, vol. 71, No. 8, pp. 1550-1555.

Schwenninger et al., "Detection of Antifungal Properties in *Lactobacillus paracasei* Subsp. *paracasei* SM20, SM29, and SM63 and Molecular Typing of the Strains," Journal of Food Protection, 2005, vol. 68, No. 1, pp. 111-119.

PCT International Search Report for Application No. PCT/EP2013/060370; Roscoe, Richard, Authorized Officer ISA/EPO; dated Oct. 14, 2013.

PCT International Report on Patentability for Application No. PCT/EP2013/060370; Wittman-Regis, Agnes, Authorized Officer; dated Nov. 25, 2014.

New Zealand Intellectual Property Office First Examination Report for Application No. 701895; Ireland, Mark, Associate Patent Examiner, dated Oct. 8, 2015.

Miescher, "Antimicrobial and Autolytic Systems of Dairy Propionibacteria," A Dissertation Submitted to Swiss Federal Institute of Technology Zurich (ETHZ) for the Degree of Technical Sciences, ETH Zürich, 1999, 7 pages.

Magnusson et al., "Broad and complex antifungal activity among environmental isolates of lactic acid bacteria," FEMS Microbiology Letters, 2003, vol. 219, No. 1, pp. 129-135.

Kantachote et al., "Characterization of the antiyeast compound and probiotic properties of a starter Lactobacillus plantarum DW3 for possible use in fermented plant beverages," Electronic Journal of Biotechnology, 2010, vol. 13, No. 5, pp. 1-15.

Hassan et al., "Antifungal activity of *Lactobacillus paracasei* ssp. *tolerans* isolated from a sourdough bread culture," International Journal of Food Microbiology, 2008, vol. 121, No. 1, pp. 112-115.

EPO Examination Report for Application No. 13 726 447.9-1410; Roscoe, Richard, Primary Examiner, dated Feb. 12, 2016.

Miescher, S., "Antimicrobial and Autolytic Systems of Dairy Propionibacteria," Thesis, Swiss Federal Institute of Technology Zurich (1999).

* cited by examiner

STRAINS OF *LACTOBACILLUS* WITH ANTIFUNGAL PROPERTIES

CROSS-REFERENCE TO RELATED PATENT APPLICATIONS

This patent claims priority as a continuation under 35 USC § 120 to U.S. patent application Ser. No. 15/380,213 (filed Dec. 15, 2016), which, in turn, claims priority as a continuation under 35 USC § 120 to U.S. patent application Ser. No. 14/402,625 (filed Nov. 20, 2014; published as US2015/0132270 on May 14, 2015), which, in turn, claims priority under 35 USC § 371 as a national phase of Int'l Patent Appl. PCT/EP2013/060370 (filed May 21, 2013; and published as Int'l Publ. No. WO2013/174792 on Nov. 28, 2013), which, in turn, claims priority to U.S. Provisional Patent Appl. No. 61/649,651 (filed May 21, 2012). The entire text of each of the above-referenced patent applications is incorporated by reference into this patent.

FIELD OF THE INVENTION

The present invention relates to novel strains of the genus *Lactobacillus* as well as preparations and compositions, such as fermentation broths, protective cultures, final food or feed product with *Lactobacillus* alone or in combination with bacteria of the genus *Propionibacterium*. The present invention further relates to methods for the controlling of growth of a contaminant, such as a bacteria, yeast or mould by using these novel strains of *Lactobacillus*.

BACKGROUND OF THE INVENTION

Yeasts and moulds play a major role in spoilage of different types of dairy products, like yogurt, sweetened and sour cream and fresh and ripened cheese types and thus can lead to high economic losses. Chemical preservatives like organic acids and their salts (e.g. sorbate and propionate) are used to preserve dairy products and protect and prolong the shelf life. Drawbacks in using chemical preservatives are the labeling requirements (often as E numbers) and potential adverse effects on the sensory properties of the foodstuff.

Lactic acid bacteria are known to produce various antimicrobial compounds, such as organic acids, hydrogen peroxide, diacetyl and bacteriocins. Lactic acid bacteria and products produced by lactic acid bacteria have been suggested as an alternative type additive to improve the shelf-life of food and animal feed. A commercial antimicrobial product, Nisaplin® (Danisco) is based on nisin purified from *Lactococcus lactis*.

EP0302300 relates to process for preparing a yeast- and mold-inhibiting low-molecular weight product by culturing a *Lactobacillus casei* species and isolating the product from the medium.

US2008286406 A1 relates to a *Lactobacillus delbrueckii* subsp. *lactis* strain having antifungal activity against mold of genus *Penicillium*, and its use in mold control in animal feed.

US2008299098 A1 relates to a *Lactobacillus johnsonii* strain and its use as a probiotic, as a prophylactic agent or as a surface treatment of materials against various human and animal pathogens.

WO2009130423 relates to a *Lactobacillus paracasei* subsp. *paracasei* strain and its use as a probiotic.

DE202006014937 relates to butterfat mixture with reduced fat content, comprises a butter and bio-protective cultures from lactic acid bacteria in the absence of preservatives.

In 1993 Valio, a Finnish dairy company described in EP 0576780 a novel microorganism strain, *Lactobacillus casei* ssp. *rhamnosus* LC-705 (deposited at Deutsche Sammlung von Mikroorganismen and Zellkulturen GmbH (DSM) as DSM 7061), having a yeast and mould controlling effect. EP 0576780 also described the use of a protective culture to inhibit fungal growth using a mixture of the *Lactobacillus casei* ssp. *rhamnosus* strain and a *Propionibacterium freudenreichii* subsp. *shermanii* strain (DSM 7067). The specific characteristic of this co-culture was that the combination of the *Lactobacillus* and the *Propionibacterium* had better antifungal activity than the *Lactobacillus rhamnosus* alone. The culture was commercialized by Wiesby under the name "Bio Profit" and renamed into HOLDBAC™ YM-B by Danisco.

EP1308506 (Swiss Federal Institute of Technology (ETH) in Zürich, Switzerland) also describes the combination of lactobacilli and propionibacteria. A *Lactobacillus paracasei* subsp. *paracasei* strain (DSM 14514) from the ETH was commercialized as a blend with *Propionibacterium freudenreichii* subsp. *shermanii* DSM 7067 from Valio under the name HOLDBAC™ YM-C.

WO 03/040349 relates to a mixture of bacteria being a non-starter culture which is free from metabolites and comprising the species *Propionibacterium jensenii* and a second bacterium selected from the genus *Lactobacillus*.

OBJECT OF THE INVENTION

It is an object of embodiments of the invention to provide improved strains of *Lactobacillus* as well as preparations and compositions, such as fermentation broths, protective cultures, final food or feed product comprising such improved *Lactobacillus* alone or in combination with bacteria of the genus *Propionibacterium*.

It is an object of embodiments of the invention to provide methods for the controlling of growth of a contaminant, such as a bacteria, yeast or mould by using these novel strains of *Lactobacillus*.

SUMMARY OF THE INVENTION

It has been found by the present inventor(s) that novel strains of *Lactobacillus* have improved properties in terms of being able to control of growth of a contaminant, such as a bacteria, yeast or mould.

So, in a first aspect the present invention relates to a bacterium of the genus *Lactobacillus* selected from the list consisting of:
 a. *Lactobacillus paracasei* DSM 25832
 b. *Lactobacillus plantarum* DSM 25833
 c. *Lactobacillus plantarum* DSM 25834
 d. *Lactobacillus plantarum* DSM 25835
 e. *Lactobacillus plantarum* DSM 25836
 f. *Lactobacillus plantarum* DSM 25837;
and functional equivalents thereof.

In a second aspect the present invention relates to a bacterial preparation, characterized in that it comprises a *Lactobacillus* selected from the list consisting of:
 a. *Lactobacillus paracasei* DSM 25832
 b. *Lactobacillus plantarum* DSM 25833
 c. *Lactobacillus plantarum* DSM 25834
 d. *Lactobacillus plantarum* DSM 25835
 e. *Lactobacillus plantarum* DSM 25836
 f. *Lactobacillus plantarum* DSM 25837;
or functional equivalents thereof, alone or in combination with a bacterium of the genus

*Propionibacterium*, with any other strain of the genus *Lactobacillus*, or with both.

In a third aspect the present invention relates to the use of bacteria of the genus *Lactobacillus* selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
or functional equivalents thereof, in the preparation of a final food or feed product.

In a further aspect the present invention relates to the use of a bacterial preparation comprising a *Lactobacillus* selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
or functional equivalents thereof, to control the growth of a contaminant, such as a bacteria, yeast or mould.

In a further aspect the present invention relates to a method of controlling the growth of a contaminant, such as bacteria, yeast or mould, characterized by using a bacterial preparation comprising a *Lactobacillus* selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
or functional equivalents thereof, alone or in combination with a bacterium of the genus *Propionibacterium*, with another strain of the bacterium *Lactobacillus*, or with both.

In some embodiments the method further comprises as step of purifying and/or concentrating said bacteria of the genus *Lactobacillus*.

In a further aspect the present invention relates to the use of a preparation of viable *Lactobacillus* bacteria selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
or functional equivalents thereof, to control the growth of a contaminant, such as a bacteria, yeast or mould.

In a further aspect the present invention relates to a method for controlling the growth of a contaminant, such as a bacteria, yeast or mould, in a composition, the method characterized by having in said composition the presence of viable *Lactobacillus* bacteria selected from the group consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
or functional equivalents thereof.

LEGENDS TO THE FIGURE

FIG. 1-8 are the results of overlayer assays. The clear zones around the LAB colonies are visible when antifungal metabolites were produced by the Lactobacilli.

FIG. 1: *Lactobacillus plantarum* DSM 25834 and its inhibitory effect on *Penicillium* sp. DCS 436.

Figure 2:

FIG. 2: *Lactobacillus plantarum* DSM 25834 and its inhibitory effect on *Penicillium* sp. DCS 1066.

Figure 3:
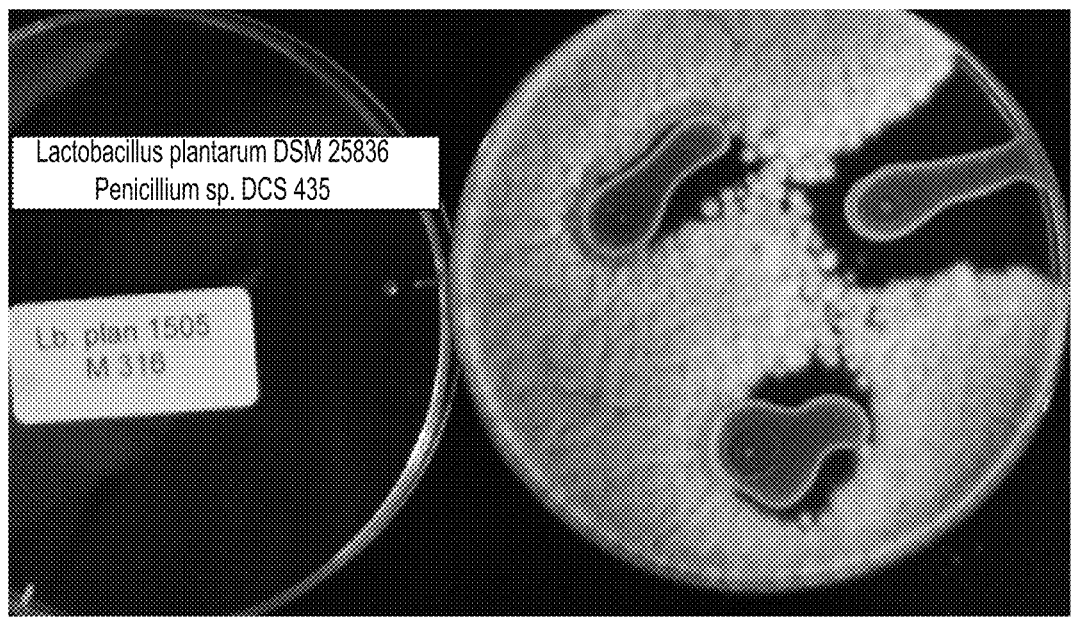

FIG. 3: *Lactobacillus plantarum* DSM 25836 and its inhibitory effect on *Penicillium* sp. DCS 435.

Figure 4:
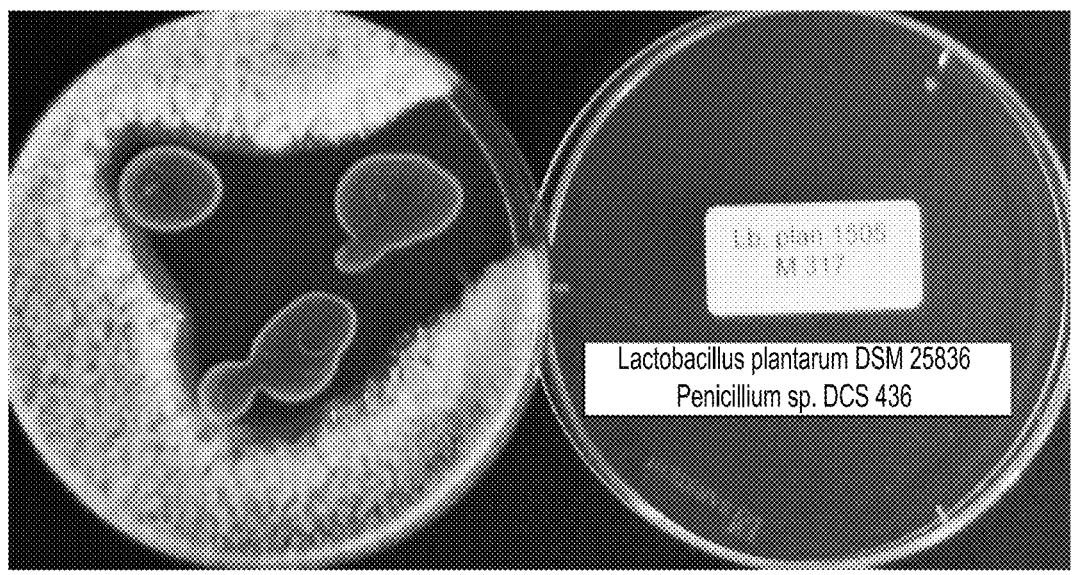

FIG. 4: *Lactobacillus plantarum* DSM 25836 and its inhibitory effect on *Penicillium* sp. DCS 436.

Figure 5:
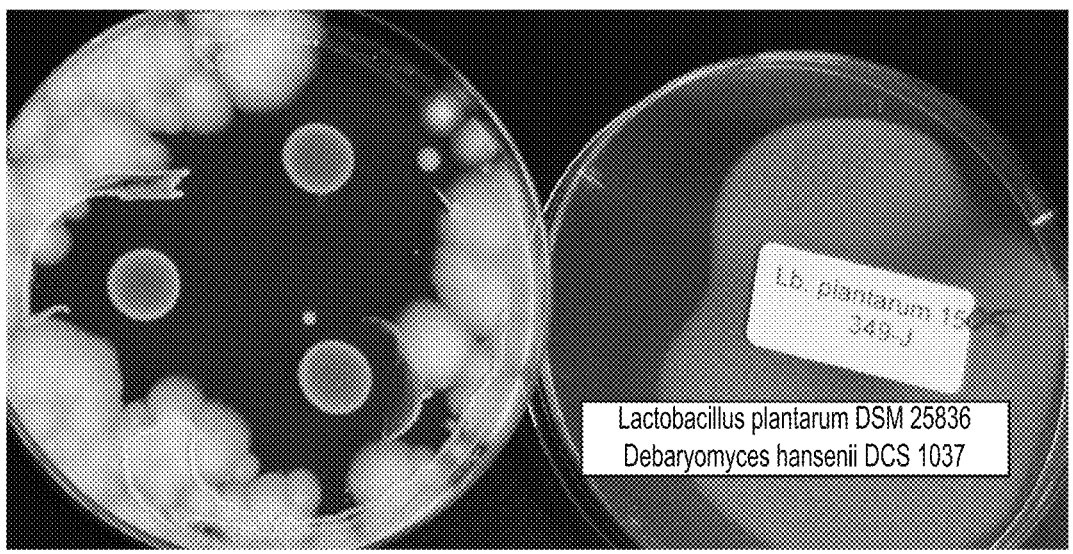

FIG. 5: *Lactobacillus plantarum* DSM 25836 and its inhibitory effect on *Debaryomyces hansenii* DCS 1037.

Figure 6:

FIG. 6: *Lactobacillus plantarum* DSM 25833 and its inhibitory effect on *Fusarium* sp. DCS 1106.

Figure 7:
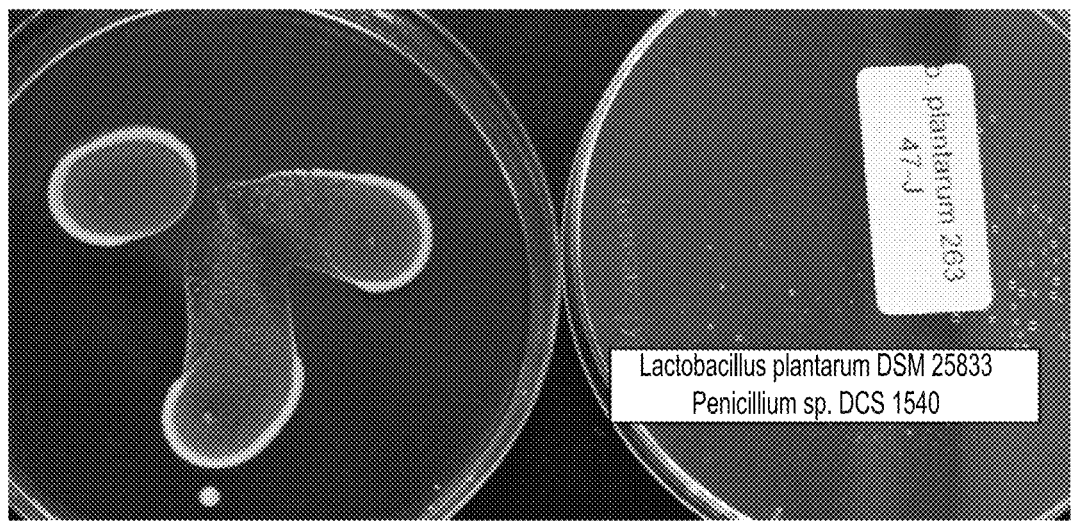

FIG. 7: *Lactobacillus plantarum* DSM 25833 and its inhibitory effect on *Penicillium* sp. DCS 1540.

Figure 8:
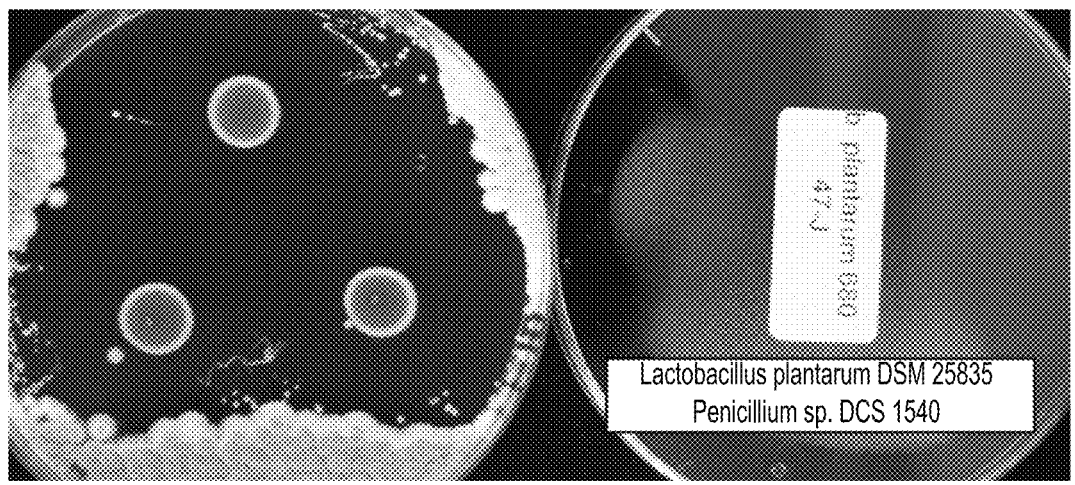

FIG. 8: *Lactobacillus plantarum* DSM 25835 and its inhibitory effect on *Penicillium* sp. DCS 1540.

DETAILED DISCLOSURE OF THE INVENTION

The present invention concerns improved strains of *Lactobacillus* having inhibition activity against bacteria, yeast and moulds. The bacteria are suitable for the preservation of goods (e.g. food or feed).

The antifungal effects of the commercial available antifungal cultures HOLDBAC™ YM-B and YM-C (DuPont, Denmark) has been demonstrated in various challenge studies in different types of fermented dairy products like yogurt, fresh cheese, sour cream and white brined cheese. Furthermore the application of HOLDBAC™ YM-B and YM-C was evaluated in internal trials in Gouda-type cheese. The results demonstrated a delayed outgrowth of spoilage moulds on the cheeses prepared with either YM-B or YM-C compared to a reference without protective culture added. It is envisioned, that the mere presence of the *Propionibacterium* strain potentially may induce the formation of antifungal metabolites by the *Lactobacillus* strain. The inventors of the present invention have demonstrated that the major part of the antifungal activity is coming from the *Lactobacillus*.

As described in the examples, the strains were screened in an agar assay.

The strains can be used to develop antifungal cultures especially for dairy applications. Using the antifungal lactobacilli of the invention, antifungal cultures based on the co-culture concept of HOLDBAC YM would be possible, for use in, e.g., yoghurt (including drinking yoghurt), sour cream, semi-hard and hard cheese, cottage cheese, fresh cheese, cream cheese, and white-brined cheese. Other food applications like e.g. sourdough may be a potential application as well as protection of feed products, such as e.g. silage.

Definitions

As used herein the term "viable" refers to bacterial cells with the potential to have an active metabolism, to survive, grow, or multiply.

As used herein the term "protective culture of *Lactobacillus*" refers to composition comprising live *Lactobacillus* (pure cultures or culture concentrates), which is not a final food product suitable for consumption, but which is added to food products with the aim of reducing risks by pathogenic or toxinogenic microorganisms. Included within this definition are compositions, such as fermentation media and concentrated preparations thereof, wherein *Lactobacillus* is grown in a suitable media.

The European Food and Feed Cultures Association (EFFCA) has characterized protective cultures as follows: "The term "Protective Cultures" has been applied to microbial food cultures (MFC) exhibiting a metabolic activity contributing to inhibit or control the growth of undesired microorganisms in food. These undesired microorganisms could be pathogenic or toxinogenic bacteria and fungi but spoilage causing species may also be included.

Protective cultures are considered as an integral part of starter cultures, which are the traditional tools of food technology used to produce fermented food such as cheese, yoghurt, certain sausages, wine etc. It is a general property of fermented foods that these possess a longer shelf life than the non-fermented raw materials (for instance cheese, has a much longer shelf-life than milk). This property is the result of the active metabolism of the fermenting culture, conducting its actions through a complex system of competition for nutrients and binding sites and by production of inhibitory metabolites like organic acids, hydrogen peroxide, diacetyl, reuterin and bacteriocins.

Depending on the specific cultures used the cultures commonly form numerous properties that are of sensory and nutritive value to the food product, too. In this way the same starter culture species used in fermentation processes have also been applied to food in order to make use of the "bioprotective" potential with or without sensory impact. For these starter cultures the term protective culture, has been applied.

Their usage is not limited to "classic" fermented foods but also plays an important role when their metabolic activities take place in food with a neutral pH and high water activity, which are subject to increased risk of growth of food pathogens. The application of "protective cultures" constitutes an additional measure to improve food hygiene and should not permit a neglecting of any measure of good manufacturing practice ensuring the high standard of food safety.

Protective cultures are an integral part of starter cultures rather than additives. It is clear that these cultures develop their protective and beneficial potential, like all starter cultures, as a result of their metabolic activity in or on the food." (EFFCA, December 2011)

The protective culture is added together with a starter culture to the food or feed matrix before the fermentation of the food or feed. Thus the protective culture undergoes the fermentation step and is able to grow and/or to be metabolic active. The starter culture is needed to produce fermented foods like yogurt, cheese and sour cream and contributes to the desired product changes in taste, texture and flavor development. In addition to this, protective cultures are added to the food to limit the growth of pathogenic or spoilage bacteria and thus reduce the risk of food poisonings and protect the shelf-life.

As used herein the term "final food or feed product" refers to a composition suitable for consumption, such as for human or animal consumption in the form of a food or feeding stuff.

As used herein the term "preparation" refers to any composition or parts thereof derived from a medium conditioned by the growth of bacteria of the genus *Lactobacillus* or an extract thereof including extracts containing one or more non-viable bacterial cell components, such as lipids, proteins or nucleic acid components derived from the bacteria of the genus *Lactobacillus*. Included within this definition of preparations are both liquid preparations as well as dry powder preparations, wherein water has been essentially removed.

The term "contaminant" as used herein refers to any unwanted and unintentional growth of any microorganism, such as bacteria, fungi, such as yeast or a mould. In some instances the contaminant may cause disease. However, often the contaminant just degrade and deteriorate the product wherein it is found and/or give an unpleasant and unwanted taste or mouth feel.

In some embodiments the contaminant is a fungi selected from the list consisting of *Penicillium* spp., *Penicillium brevicompactum*, *Penicillium solitum*, *Penicillium glabrum*, *Penicillium corylophilum*, *Penicillium roqueforti*, *Aspergillus* sp., *Aspergillus ochraceus*, *Aspergillus parasiticus*, *Aspergillus versicolor*, *Aspergillus niger*, *Eurotium* spp., *Fusarium* spp., *Candida* spp., *Candida colliculosa*, *Candida famata*, *Candida guilliermondii*, *Candida kefyr*, *Candida lambica*, *Candida lipolytica*, *Candida lusitaniae*, *Candida sake*, *Candida sphaerica*, *Candida parapsilosis*, *Candida pelliculosa*, *Candida rugosa*, *Candida zeylanoides*, *Debaryomyces* spp., *Debaryomyces hansenii*, *Kluyveromyces* spp., *Kluyveromyces marxianus*, *Rhodotorula* spp., *Rhodotorula mucilaginosa*, *Saccharomyces* spp., *Saccharomyces cerevisiae*, *Saccharomyces servazzii*, and *Geotrichum* spp., *Geotrichum candidum*.

In some embodiments the contaminant is a bacteria different from the specific *Lactobacillus* strain used in the methods according to the invention, selected from the list consisting of *Listeria monocytogenes*, *Pseudomonas* sp., *Staphylococcus aureus*, *Bacillus* sp., *Lactobacillus* sp., *Leuconostoc* sp., *Clostridium* sp. Enterobacteriaceae like *Citrobacter* sp., *Enterobacter* sp., *Escherichia* sp., *Klebsiella* sp., *Salmonella* sp.

Lactobacillus

As used herein the term "any other strain of the genus *Lactobacillus*" or "any other strain of *Lactobacillus*" refers to any strain of the genus *Lactobacillus*, which is not a strain of *Lactobacillus* selected from the list consisting of: *Lactobacillus paracasei* DSM 25832, *Lactobacillus plantarum* DSM 25833, *Lactobacillus plantarum* DSM 25834, *Lactobacillus plantarum* DSM 25835, *Lactobacillus plantarum* DSM 25836 and *Lactobacillus plantarum* DSM 25837, such as strains of *Lactobacillus* that may be used for the production of yogurt, cheese, sauerkraut, pickles, beer, wine, cider, kimchi, cocoa, and other fermented foods, as well as animal feeds, such as silage. The term *Lactobacillus* is intended to encompass organisms described in (http://www.bacterio.cict.fr/l/Lactobacillus.html), and in particular including *L. acetotolerans*, *L. acidifarinae*, *L. acidipiscis*, *L. acidophilus*, *L. agilis*, *L. algidus*, *L. alimentarius*, *L. amylolyticus*, *L. amylophilus*, *L. amylotrophicus*, *L. amylovorus*, *L. animalis*, *L. antri*, *L. apodemi*, *L. aviarius*, *L. bifermentans*, *L. brevis*, *L. buchneri*, *L. camelliae*, *L. casei*, *L. catenaformis*, *L. ceti*, *L. coleohominis*, *L. coffinoides*, *L. composti*, *L. concavus*, *L. coryniformis*, *L. crispatus*, *L. crustorum*, *L. curvatus*, *L. delbrueckii* subsp. *delbrueckii*, *L. delbrueckii* subsp. *bulgaricus*, *L. delbrueckii* subsp. *lactis*, *L. dextrinicus*, *L. diolivorans*, *L. equi*, *L. equigenerosi*, *L. farraginis*, *L. farciminis*, *L. fermentum*, *L. fomicalis*, *L. fructivorans*, *L. frumenti*, *L. fuchuensis*, *L. gallinarum*, *L. gasseri*, *L. gastricus*, *L. ghanensis*, *L. graminis*, *L. hammesii*, *L. hamsteri*, *L. harbinensis*, *L. hayakitensis*, *L. helveticus*, *L. hilgardii*, *L. homohiochii*, *L. iners*, *L. ingluviei*, *L. intestinalis*, *L. jensenii*, *L. johnsonii*, *L. kalixensis*, *L. kefiranofaciens*, *L. kefiri*, *L.*

*kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracoffinoides, L. parafarraginis, L. parakefiri, L. paralimentarius, L. paraplantarum, L. pentosus, L. perolens, L. plantarum, L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae,* and *L. zymae,* as well as variants thereof.

The term *Lactobacillus* is intended to encompass any specific *Lactobacillus* strain described in EP0576780, EP1308506 EP1796698, EP2245943, EP1530642, EP1740726, WO 03/040349 WO/2006/032542, WO/2007/132359, WO/2004/013343, and WO/2010/081138.

In some embodiments the any other *Lactobacillus* strain is selected from *Lactobacillus paracasei* subsp. *paracasei* DSM 14514, and *Lactobacillus rhamnosus* DSM 7061.

*Propionibacterium*

As used herein the term "a strain of the bacterium *Propionibacterium*" refers to any strain of the genus *Propionibacterium* including the species *Propionibacterium acidifaciens, Propionibacterium acidipropionici, Propionibacterium acnes, Propionibacterium australiense, Propionibacterium avidum, Propionibacterium cyclohexanicum, Propionibacterium freudenreichii* subsp. *freudenreichii, Propionibacterium freudenreichii* subsp. *shermanii, Propionibacterium granulosum, Propionibacterium jensenii, Propionibacterium microaerophilum, Propionibacterium propionicum,* and *Propionibacterium thoenii,* as well as variants thereof. The term is intended to encompass specific *Propionibacterium* strains described in the present disclosure and in any of EP0576780, EP1308506, WO03/040349, and U.S. Pat. No. 4,728,516, including *Propionibacterium freudenreichii* subsp. *shermanii* DSM 7067.

Specific Embodiments of the Invention

In some embodiments the bacterial preparation according to the present invention is a cell suspension in fermentation broth, alone or in combination with a bacterium of the genus *Propionibacterium* or any other strain of *Lactobacillus.*

In some embodiments the bacterial preparation according to the present invention comprises a strain of *Lactobacillus* selected from *Lactobacillus paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; or a combination of any thereof.

In some embodiments, the bacterial preparation further comprises a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus paracasei* DSM 25832 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus plantarum* DSM 25833 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus plantarum* DSM 25834 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus plantarum* DSM 25835 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus plantarum* DSM 25836 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Lactobacillus plantarum* DSM 25837 and a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

In some embodiments the bacterial preparation according to the present invention is concentrated.

In some embodiments the bacterial preparation according to the present invention is freeze-dried or frozen.

In some embodiments the bacterial preparation according to the present invention is characterized in that it additionally comprises conventional agents used for yeast and mould control, such as propionate or phenylalanine.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final food or feed product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition or preparation according to the present invention is a protective culture of *Lactobacillus*.

In some embodiments the composition or preparation according to the present invention is a final food or feed product.

In some embodiments the composition according to the present invention is with or without cell remnants of said bacteria of the genus *Propionibacterium*.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition or preparation according to the present invention is used for the preparation of a food product of feed product, such as a milk product. In some embodiments the food product is selected from the group consisting of dairy products, yoghurt, drinking yogurt, cheese, such as fresh cheese, cream cheese, cottage cheese, semi-soft and soft cheese, semi-hard and hard cheese, white brine cheese, sour milk products, and sour cream, sauerkraut, pickles, beer, wine, cider, kimchi, cocoa, sour dough and other fermented foods, as well as animal feeds, such as silage.

In some embodiments according to the present invention, the "any other bacteria of the genus *Lactobacillus*" is selected from *Lactobacillus paracasei* DSM 14514 and *Lactobacillus rhamnosus* DSM 7061.

Numbered embodiments according to the invention:

1. A bacterium of the genus *Lactobacillus* selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
   or functional equivalents thereof.

2. A bacterial preparation, characterized in that it comprises a *Lactobacillus* selected from the list consisting of:
   a. *Lactobacillus paracasei* DSM 25832
   b. *Lactobacillus plantarum* DSM 25833
   c. *Lactobacillus plantarum* DSM 25834
   d. *Lactobacillus plantarum* DSM 25835
   e. *Lactobacillus plantarum* DSM 25836
   f. *Lactobacillus plantarum* DSM 25837;
   or functional equivalents thereof, alone or in combination with a bacterium of the genus *Propionibacterium*, with any other strain of the genus *Lactobacillus*, or with both.

3. A bacterial preparation according to embodiment 2, which is a cell suspension in fermentation broth, alone or in combination with a bacterium of the genus *Propionibacterium*, with another strain of *Lactobacillus*, or with both.

4. A bacterial preparation according to any one of embodiments 2-3, characterized in that it comprises a strain of *Propionibacterium* selected from *Propionibacterium acidipropionici* DSM 25845; *Propionibacterium freudenreichii* DSM 25846; *Propionibacterium freudenreichii* DSM 25847; *Propionibacterium thoenii* DSM 25848; and *Propionibacterium thoenii* DSM 25849, and *Propionibacterium freudenreichii* subsp. *shermanii* DSM 7067, or a combination of any thereof.

5. A bacterial preparation according to any one of embodiments 2-4, which preparation is concentrated.

6. A bacterial preparation according to any one of embodiments 2-4, which preparation is freeze-dried.

7. A bacterial preparation according to any one of embodiments 2-6, characterized in that it additionally comprises conventional agents used for yeast and mould control, such as propionate or phenylalanine.

8. Use of bacteria of the genus *Lactobacillus* selected from the list consisting of:

a. *Lactobacillus paracasei* DSM 25832
b. *Lactobacillus plantarum* DSM 25833
c. *Lactobacillus plantarum* DSM 25834
d. *Lactobacillus plantarum* DSM 25835
e. *Lactobacillus plantarum* DSM 25836
f. *Lactobacillus plantarum* DSM 25837;
or functional equivalents thereof, in the preparation of a final food or feed product.

9. Use of a bacterial preparation comprising a *Lactobacillus* selected from the list consisting of:
a. *Lactobacillus paracasei* DSM 25832
b. *Lactobacillus plantarum* DSM 25833
c. *Lactobacillus plantarum* DSM 25834
d. *Lactobacillus plantarum* DSM 25835
e. *Lactobacillus plantarum* DSM 25836
f. *Lactobacillus plantarum* DSM 25837;
or functional equivalents thereof, to control the growth of a contaminant, such as a bacteria, yeast or mould.

10. A method of controlling the growth of a contaminant, such as bacteria, yeast or mould, characterized by using a bacterial preparation comprising a *Lactobacillus* selected from the list consisting of:
a. *Lactobacillus paracasei* DSM 25832
b. *Lactobacillus plantarum* DSM 25833
c. *Lactobacillus plantarum* DSM 25834
d. *Lactobacillus plantarum* DSM 25835
e. *Lactobacillus plantarum* DSM 25836
f. *Lactobacillus plantarum* DSM 25837;
or functional equivalents thereof, alone or in combination with a bacterium of the genus *Propionibacterium*, with another strain of the genus *Lactobacillus*, or with both.

11. Use of a preparation of viable *Lactobacillus* bacteria selected from the list consisting of:
a. *Lactobacillus paracasei* DSM 25832
b. *Lactobacillus plantarum* DSM 25833
c. *Lactobacillus plantarum* DSM 25834
d. *Lactobacillus plantarum* DSM 25835
e. *Lactobacillus plantarum* DSM 25836
f. *Lactobacillus plantarum* DSM 25837;
or functional equivalents thereof, to control the growth of a contaminant, such as a bacteria, yeast or mould.

12. A method for controlling the growth of a contaminant, such as bacteria, yeast or mould, in a composition, the method characterized by having in said composition the presence of a viable *Lactobacillus* bacteria of a strain selected from the group consisting of:
a. *Lactobacillus paracasei* DSM 25832
b. *Lactobacillus plantarum* DSM 25833
c. *Lactobacillus plantarum* DSM 25834
d. *Lactobacillus plantarum* DSM 25835
e. *Lactobacillus plantarum* DSM 25836
f. *Lactobacillus plantarum* DSM 25837;
or functional equivalents thereof.

EXAMPLE 1

Lactobacilli Test Strains
The following lactobacilli strains were used:
*Lactobacillus paracasei* DSM 25832
*Lactobacillus plantarum* DSM 25833
*Lactobacillus plantarum* DSM 25834
*Lactobacillus plantarum* DSM 25835
*Lactobacillus plantarum* DSM 25836
*Lactobacillus plantarum* DSM 25837
Cultivation of Lactobacilli
The lactobacilli were propagated in MRS broth (Oxoid Limited, Basingstoke, United Kingdom) at 30° C. A passage was done by adding 0.1 ml from the pre-cultures to 10 ml MRS broth, cultivation as described above. The cultures were kept at 4-6° C. prior to use.
Yeast and Mould Indicator Strains
The yeast and mould strains are listed in Tables 1 and 2.

TABLE 1

List of yeast strains used in the screening for antifungal activity

| Strain Number | Strain name | Reference |
| --- | --- | --- |
| 205-J | *Candida lipolytica* | DuPont A/S[1] |
| DCS 605 | *Debaryomyces hansenii* | DSM 70238[2] |
| DCS 1037 | *Debaryomyces hansenii* | DuPont A/S |
| DSC 1055 | *Candida sake* | DuPont A/S |
| DSC 1057 | *Candida sake* | DuPont A/S |
| DSC 1063 | *Rhodotorula mucilaginosa* | DuPont A/S |
| DCS 1087 | *Rhodotorula mucilaginosa* | CFSQE 63[3] |
| DCS 1088 | *Candida pulcherrima* | Miescher[4] |
| DCS 1089 | *Kluyveromyces marxianus* | CBS 1555[5] |
| DCS 1228 | *Saccharomyces cerevisiae* | DuPont A/S |
| DCS 1518 | *Candida parapsilosis* | DuPont A/S |

1) Danisco Nutrition Biosciences ApS, Brabrand, Denmark
2) Deutsche Sammlung von Mikroorganismen and Zellkulturen GmbH, Braunschweig, Germany
3) Magnusson, J., Strom, K., Roos, S., Sjögren, J., and Schnürer, J. 2003. Broad and complex antifungal activity among environmental isolates of lactic acid bacteria. FEMS Microbiology Letters 219: 129-135.
4) Miescher, S. 1999. Antimicrobial and autolytic systems of dairy propionibacteria. PhD thesis No. 13486. ETH Zürich, Switzerland
5) Centraalbureau voor Schimmelcultures, Utrecht, The Netherlands Prior to use, the yeast strains were cultivated in a broth consisted of 2% glucose (vwr, Herlev, Denmark), 0.5% yeast extract (Oxoid Limited, Basingstoke, United Kingdom) and 0.01% peptone from casein (Oxoid) dissolved in a potassium di-hydrogen phosphate solution (312 µmol/l, pH 7.20±0.10). Sterile glycerol was added in a concentration of 33% v/v to the medium with grown yeast before storage in cryo tubes at −80° C. After freezing the yeast cultures were enumerated on malt extract agar (Oxoid).

TABLE 2

List of mould strains used in the screening for antifungal activity

| Strain Number | Strain name | Origin |
| --- | --- | --- |
| DCS 434 | *Penicillium* sp. | DuPont A/S |
| DCS 435 | *Penicillium* sp. | DuPont A/S |
| DCS 436 | *Penicillium* sp. | DuPont A/S |
| DCS 437 | *Penicillium* sp. | DuPont A/S |
| DCS 708 | *Aspergillus ochraceus* | CBS 116.39 |
| DCS 709 | *Aspergillus parasiticus* | CBS 100926 |
| DCS 1065 | *Penicillium* sp. | DuPont A/S |
| DCS 1066 | *Penicillium* sp. | DuPont A/S |
| DCS 1069 | *Aspergillus versicolor* | DSM 63292 |
| DCS 1099 | *Eurotium* sp. | DTU 123[6] |
| DCS 1105 | *Fusarium* sp. | DTU 40496 |
| DCS 1106 | *Fusarium* sp. | DTU 40872 |
| DCS 1540 | *Penicillium* sp. | DuPont A/S |
| DCS 1541 | *Penicillium* sp. | DuPont A/S |
| DCS 1558 | *Penicillium* sp. | DuPont A/S |

6) Danmarks Tekniske Universitet, Lyngby, Denmark
The mould strains were cultivated on malt extract agar slants (Oxoid) until sporulation was visible. The spores were harvested by adding twice 5 ml sterile tap water supplemented with 0.01% Tween 80 (Merck). Sterile glycerol was added in a concentration of 33% v/v to the spore solutions before storage in cryo tubes at −80° C. A spore count was made after freezing on malt extract agar (Oxoid).

Overlayer Assay

The lactobacilli test strains were spot inoculated (three spots per plate) on MRS agar. The plates were incubated at 30° C.

The plates with grown colonies of the lactobacilli were overlaid with malt extract soft agar consisted of 2% malt extract broth (Oxoid) and 0.8% agar agar (Merck KGaA, Darmstadt, Germany) tempered to 47° C. containing either $10^4$ yeast cells/ml or $10^4$ mould spores/ml. The overlaid plates were incubated for 3-5 days at 25° C. and inspected for inhibition zones around the test colonies. As a growth control agar plates without spotted test strains were prepared for each indicator organisms. The area of the zones was graded as follows:

| | |
|---|---|
| No inhibition, plate fully overgrown | − |
| No fungal growth on the spot | (+) |
| No fungal growth for 5 mm around the spot | + |
| No fungal growth for 10 mm around the spot | ++ |
| No fungal growth for 15 mm around the spot | +++ |
| No fungal growth above 15 mm around the spot | ++++ |

Results

Six lactobacilli were tested for antifungal activities. Therefore, the strains were spot inoculated on MRS agar plates on which the fungi listed in table 1 and 2 were applied incorporated in malt extract soft agar. The plates were stored at 25° C. and inspected for inhibition zones around the lactobacilli colonies.

All six tested lactobacilli showed antifungal activity in the applied overlayer assay as summarised in Table 3. Lactobacillus plantarum DSM 25837 was assayed in a second trial and not all fungi were used thus some results are not available on this strain.

In general, the lactobacilli showed different inhibition spectra. The highest activities were detected with Lactobacillus plantarum DSM 25833 followed by Lactobacillus plantarum DSM 25834 and Lactobacillus plantarum DSM 25836. Weaker activities were observed with Lactobacillus paracasei DSM 25832 compared to the Lactobacillus plantarum strains.

TABLE 3

Antifungal activities of selected *Lactobacillus* strains in an overlayer assay

| | Lb. paracasei DSM 25832 | Lb. plantarum DSM 25833 | Lb. plantarum DSM 25834 | Lb. plantarum DSM 25835 | Lb. plantarum DSM 25836 | Lb. plantarum DSM 25837 |
|---|---|---|---|---|---|---|
| Candida lipolytica 205-J | +++ | ++ | ++ | ++ | + | n.d. |
| Debaryomyces hansenii DCS 605 | +++ | ++++ | ++ | ++ | ++ | n.d. |
| Debaryomyces hansenii DCS 1037 | ++ | ++ | ++ | ++ | ++ | n.d. |
| Candida sake DCS 1055 | + | +++ | +++ | ++ | ++ | ++++ |
| Candida sake DCS 1057 | ++ | +++ | ++ | +++ | +++ | n.d. |
| Rhodotorula mucilaginosa DCS 1063 | +++ | +++ | +++ | +++ | +++ | ++ |
| Rhodotorula mucilaginosa DCS 1087 | − | ++ | ++ | + | + | + |
| Candida pulcherrima DCS 1088 | − | + | + | (+) | + | n.d. |
| Kluyveromyces marxianus DCS 1089 | − | + | + | + | − | − |
| Saccharomyces cerevisiae DCS 1228 | ++ | ++ | +++ | ++ | + | n.d. |
| Candida parapsilosis DCS 1518 | − | ++ | ++ | ++ | + | n.d. |
| Penicillium sp. DCS 434 | + | + | ++ | + | ++ | n.d. |
| Penicillium sp. DCS 435 | + | ++ | + | + | ++ | n.d. |
| Penicillium sp. DCS 436 | ++ | ++ | +++ | +++ | +++ | n.d. |
| Penicillium sp. DCS 437 | + | + | (+) | (+) | + | n.d. |
| Aspergillus ochraceus DCS 708 | +++ | ++++ | +++ | ++ | +++ | ++ |

TABLE 3-continued

Antifungal activities of selected *Lactobacillus* strains in an overlayer assay

| | Lb. paracasei DSM 25832 | Lb. plantarum DSM 25833 | Lb. plantarum DSM 25834 | Lb. plantarum DSM 25835 | Lb. plantarum DSM 25836 | Lb. plantarum DSM 25837 |
|---|---|---|---|---|---|---|
| *Aspergillus parasiticus* DCS 709 | (+) | (+) | (+) | (+) | + | (+) |
| *Penicillium* sp. DCS 1065 | +++ | ++++ | ++++ | +++ | ++++ | +++ |
| *Penicillium* sp. DCS 1066 | ++ | ++++ | ++++ | +++ | +++ | +++ |
| *Aspergillus versicolor* DCS 1069 | ++++ | ++++ | ++++ | ++++ | ++++ | +++ |
| *Eurotium* sp. DCS 1099 | + | ++++ | ++++ | + | ++++ | +++ |
| *Fusarium* sp. DCS 1105 | +++ | ++++ | ++++ | ++++ | ++++ | +++ |
| *Fusarium* sp. DCS 1106 | +++ | ++++ | ++++ | ++++ | ++++ | ++++ |
| *Penicillium* sp. DCS 1540 | ++ | ++++ | ++++ | +++ | ++++ | + |
| *Penicillium* sp. DCS 1541 | + | ++++ | ++ | ++ | ++ | ++ |
| *Penicillium* sp. DCS 1558 | ++++ | ++++ | ++++ | ++++ | ++++ | ++++ | n.d.: not determined

EXAMPLE 2

Investigation of Antifungal Activities of *Lactobacillus paracasei* Subsp. *Paracasei* DSM 14514 in an Agar Assay The frozen concentrated samples of *Lactobacillus paracasei* subsp. *paracasei* DSM 14514 are evaluated for antifungal activity using an agar assay. A reference sample without antifungal cultures is included for comparison in the evaluation. The antifungal activity is assessed using the indicator strains listed in table 1.

TABLE 1

List of yeast and mould strains used in the agar assay

| Strain Number | Strain name | Reference |
|---|---|---|
| DCS 605 | *Debaryomyces hansenii* | DSM 70238[1] |
| DCS 1065 | *Penicillium* sp. | DuPont A/S[2] |
| DCS 1540 | *Penicillium* sp. | DuPont A/S |
| DCS 1541 | *Penicillium* sp. | DuPont A/S |

1) Deutsche Sammlung von Mikroorganismen und Zellkulturen GmbH, Braunschweig, Germany Prior to use, *Debaryomyces hansenii* DCS 605 is grown in a broth consisted of 2% glucose (vwr, Herlev, Denmark), 0.5% yeast extract (Oxoid Limited, Basingstoke, United Kingdom) and 0.01% peptone from casein (Oxoid) dissolved in a potassium di-hydrogen phosphate solution (312 µmol/l, pH 7.20±0.10). Sterile glycerol is added in a concentration of 33% v/v to the medium with grown yeast before storage in cryo tubes at −80° C. After freezing the yeast culture is enumerated on malt extract agar (Oxoid). *Penicillium* sp. DCS 1065, *Penicillium* sp. DCS 1540 and *Penicillium* sp. DCS 1541 are grown on malt extract agar slants (Oxoid) until sporulation is visible. The spores are harvested by adding twice 5 ml sterile tap water supplemented with 0.01% Tween 80 (Merck). Sterile glycerol is added in a concentration of 33% v/v to the spore solutions before storage in cryo tubes at −80° C. A spore count is made after freezing on malt extract agar (Oxoid). Portions of 750 g commercial available UHT milk with 3.5% fat are acidified with a commercial yogurt starter culture. The yogurt starter culture is consisting of strains of *Streptococcus thermophilus* and *Lactobacillus delbrückii* subsp. *bulgaricus* (Danisco A/S, Denmark). Test samples are inoculated additionally with the protective strains to give a level of $5.0 \cdot 10^6$ CFU/g. The fermentation is done for about 7-9 hours at 42° C. until a pH of 4.50 is reached in the yogurt samples. The samples are shaken vigorously and 650 g yogurt is weighed in a sterile bottle. Afterwards 325 g of an agar solution consisting of 25 g agar agar (Merck) per litre, tempered to 47° C. is added to the yogurt and the bottles were shaken gently to get a homogenous mixture of yogurt and agar. The yogurt-agar mixture is poured into petri-dishes. After solidification of the yogurt agar, diluted yeast solutions and mould spore solutions are spotted on the agar plates and the growth of the indicator strains on the plates with and without antifungal cultures is compared after incubation at 25° C. The yeast strain *Debaryomyces hansenii* DCS 605 is spotted in concentrations of $5.0 \cdot 10^1$ CFU/spot, $5.0 \cdot 10^2$ CFU/spot and $5.0 \cdot 10^3$ CFU/spot in triplicates on the plates. The mould strains *Penicillium* sp. DCS 1540, *Penicillium* sp. 1541 and *Penicillium* sp. DCS 1065 are spotted in a concentration of 20 spores/spot on the plates. The inhibition activity of the samples is calculated by comparing the growth of the moulds on the unprotected reference samples with the growth on the samples produced with protective strains added according the following equation:

$$\text{Inhibition activity}[\%] = 100 - \left[ \frac{\text{Colony diameter on plate with protective culture}}{\text{Colony diameter on reference plate}} * 100 \right]$$

EXAMPLE 3

Investigation of Antifungal Activities in a Cheese Model System

The frozen concentrated samples of *Lactobacillus plantarum* DSM 25833 were evaluated for antifungal activity using a cheese model system. A reference sample without antifungal cultures was included for comparison in the evaluation. The antifungal activity was assessed using the indicator strains listed in table 2.

TABLE 2

List of mould strains used

| Strain Number | Strain name | Reference |
|---|---|---|
| DCS 1540 | *Penicillium* sp. | DuPont A/S |
| DCS 1541 | *Penicillium* sp. | DuPont A/S |
| DCS 1558 | *Penicillium* sp. | DuPont A/S |

*Penicillium* sp. DCS 1540, *Penicillium* sp. DCS 1541 and *Penicillium* sp. DCS 1558 were grown on malt extract agar slants (Oxoid) until sporulation was visible. The spores were harvested by adding twice 5 ml sterile tap water supplemented with 0.01% Tween 80 (Merck). Sterile glycerol was added in a concentration of 33% v/v to the spore solutions before storage at −80° C. A spore count was made after freezing on malt extract agar (Oxoid). The cheese model was set-up with portions of 500 ml un-homogenised milk. The milk was filled in centrifuge bottles and heated to 32° C. The milk was inoculated with a commercial available mesophilic cheese starter culture. The cheese starter culture was consisting of strains of *Lactococcus lactis* (Danisco A/S, Denmark). Test samples were additional inoculated with the protective strains to give a level of 5.0·10$^6$ CFU/ml. The milk was coagulated with commercial available liquid animal rennet (Danisco A/S, Denmark). The curd was cut into cubes of roughly 1 cm×1 cm×1 cm. The mixture of whey-curd particles was agitated for 20 min on a rolling stirrer at 10 rpm. Forty percent (approx. 200 ml) of whey was discarded and replaced by an equal volume of sterile water at 32° C. The mixture was stirred for additional 10 min as described above. Afterwards the bottles were centrifuged at 300 g for 10 min at room temperature in a centrifuge equipped with a swinging bucket rotor. Following, the whey was discarded and the bottles centrifuged at 1400 g for 1 h at 30° C. The curd was inverted in the same container, the whey discarded and a final centrifugation carried out as described above for 30 min. The miniature cheeses were kept in their containers placed in the water-bath at 32° C. until a pH of about 5.2 was reached. The cheeses were salted for 5 min by pouring 45 ml of sterile saturated brine (330 g/l NaCl; pH adjusted to 5.4; 12° C.) into the bottle. Following, the cheeses were placed in a sterile box fitted with a grid to facilitate whey draining and stored overnight at 12° C. On the next day the cheeses were vacuum packaged and let to ripen at 12° C. for 28 days. After ripening, the cheeses were surface inoculated with spore solutions of three different mould strains. The mould strains *Penicillium* sp. DCS 1540, *Penicillium* sp. DCS 1541 and *Penicillium* sp. DCS 1558 were spotted in concentrations of 5 spores/spot, 10 spores/spot and 50 spores/spot in triplicates on the cheeses. The cheeses were incubated at 12° C. and growth of the moulds was examined visually.

Results:

Antifungal Activities of *Lactobacillus plantarum* DSM 25833 in a Cheese Model System A trial in a cheese model system was set-up with different protective cultures. The antifungal strains were added to un-homogenised milk at initial levels of 5.0·10$^6$ CFU/g. The milk was acidified with a commercial cheese starter culture, coagulated with commercial available liquid animal rennet and the curd was cut in cubes. Whey was removed by centrifugation and the cheeses were pressed and salted and afterwards ripened for 28 days. After ripening, the cheeses were surface inoculated with spore solutions of three different mould strains. The mould strains *Penicillium* sp. DCS 1540, *Penicillium* sp. DCS 1541 and *Penicillium* sp. DCS 1558 were spotted in concentrations of 5, 10 and 50 spores in triplicates on the cheeses. The cheeses were incubated at 12° C. and growth of the moulds was examined visually. It was noted each time when one of the nine spots on the cheese surface showed visible growth of the mould. The average shelf life of the cheeses was calculated by taking the average of the storage days when mould growth was visible on the nine spots per cheese surface. The results are displayed in table 5.

TABLE 5

Average shelf life of experimental cheeses prepared with and without antifungal cultures

| | Reference | Lb. plantarum DSM 25833 |
|---|---|---|
| | Average shelf life [d] | |
| *Penicillium* sp. DCS 1540 | 6 | 24[1] |
| *Penicillium* sp. DCS 1541 | 7 | 16 |
| *Penicillium* sp. DCS 1558 | 12 | 61[1,2] |

[1]Mould growth not visible on all nine spots at the end of the experiment
[2]Trial terminated after 61 days The addition of *Lactobacillus plantarum* DSM 25833 to the model cheeses delayed the outgrowth of the indictor moulds compared to the reference sample without antifungal cultures added.

The invention claimed is:

1. A method of preparing a fermented final food or feed product,
   comprising adding to a food or feed matrix, together with a starter culture, *Lactobacillus plantarum* DSM 25833 bacteria or a bacterial preparation comprising *Lactobacillus plantarum* DSM 25833 bacteria, in the preparation of a fermented final food or feed product, wherein the *Lactobacillus plantarum* DSM 25833 bacteria inhibit fungal growth in the fermented final food or feed product.

2. The method according to claim 1, wherein the *Lactobacillus plantarum* DSM 25833 bacteria is added as a bacterial preparation also comprising a bacterium of the genus *Propionibacterium* or any other strain of the genus *Lactobacillus* or both a bacterium of the genus *Propionibacterium* and any other strain of the genus *Lactobacillus*.

3. The method according to claim 2, wherein the bacterium of the genus *Propionibacterium* is selected from the group consisting of *Propionibacterium acidipropionici* DSM 25845, *Propionibacterium freudenreichii* DSM 25846, *Propionibacterium freudenreichii* DSM 25847, *Propionibacterium thoenii* DSM 25848, and *Propionibacterium thoenii* DSM 25849.

4. The method according to claim 2, wherein said *Lactobacillus plantarum* DSM 25833 bacteria is added as a freeze-dried bacterial preparation.

5. The method according to claim 2, wherein the bacterial preparation additionally comprises a conventional agent used for yeast or mold control.

6. The method according to claim 5, wherein the conventional agent used for yeast or mold control is selected from the group consisting of propionate and phenylalanine.

7. A method according to claim 1, wherein the starter culture is a yogurt starter culture.

8. A method according to claim 1, wherein the starter culture comprises *Streptococcus thermophilus*.

9. A method according to claim 1, wherein the starter culture comprises *Lactobacillus delbrueckii* subsp. *bulgaricus*.

10. A method according to claim 1, wherein the starter culture is a cheese starter culture.

11. A method according to claim 1, wherein the starter culture comprises *Lactococcus lactis*.

12. A fermented final food or feed product obtained by a method according to claim 1.

13. The fermented final food or feed product according to claim 12, selected from the group consisting of dairy products, yoghurt, drinking yogurt, cheese, sour milk products, sour cream, sauerkraut, pickles, beer, wine, cider, kimchi, cocoa, sour dough, other fermented foods, animal feeds, and silage.

14. A fermented final food or feed product comprising a starter culture and viable *Lactobacillus plantarum* DSM 25833 bacteria, wherein the *Lactobacillus plantarum* DSM 25833 bacteria inhibit fungal growth in the fermented final food or feed product.

15. The fermented final food or feed product according to claim 14, selected from the group consisting of dairy products, yoghurt, drinking yogurt, cheese, sour milk products, sour cream, sauerkraut, pickles, beer, wine, cider, kimchi, cocoa, sour dough, other fermented foods, animal feeds, and silage.

* * * * *